US008546386B2

(12) United States Patent
Green et al.

(10) Patent No.: US 8,546,386 B2
(45) Date of Patent: *Oct. 1, 2013

(54) CORROSION AND MICROBIAL CONTROL IN HYDROCARBONACEOUS COMPOSITIONS

(75) Inventors: G. David Green, Cary, IL (US); Sheila M. Tinetti, Vernon Hills, IL (US); Patrick E. Brutto, Bloomingdale, IL (US); John Pohlman, Skokie, IL (US)

(73) Assignees: Dow Global Technologies LLC; ANGUS Chemical Company

( * ) Notice: Subject to any disclaimer, the term of this patent is extended or adjusted under 35 U.S.C. 154(b) by 164 days.

This patent is subject to a terminal disclaimer.

(21) Appl. No.: 12/988,550

(22) PCT Filed: Apr. 29, 2009

(86) PCT No.: PCT/US2009/042034
§ 371 (c)(1),
(2), (4) Date: Oct. 19, 2010

(87) PCT Pub. No.: WO2009/140062
PCT Pub. Date: Nov. 19, 2009

(65) Prior Publication Data
US 2011/0041387 A1 Feb. 24, 2011

Related U.S. Application Data

(60) Provisional application No. 61/053,412, filed on May 15, 2008.

(51) Int. Cl.
*A61K 31/5377* (2006.01)
*C07D 265/30* (2006.01)

(52) U.S. Cl.
USPC .......................... 514/231.8; 544/106

(58) Field of Classification Search
USPC .................. 514/241, 183, 231.8; 544/106
See application file for complete search history.

(56) References Cited

U.S. PATENT DOCUMENTS

| 2,164,271 | A | 6/1939 | Hass et al. |
| 2,695,222 | A * | 11/1954 | Chenicek et al. ............... 44/434 |
| 3,247,054 | A | 4/1966 | Hodge et al. |
| 4,074,013 | A | 2/1978 | Koch et al. |
| 4,166,725 | A | 9/1979 | Amick |
| 4,708,720 | A | 11/1987 | Grangette et al. |
| 4,877,552 | A | 10/1989 | Haring |
| 4,925,582 | A * | 5/1990 | Bennett ......................... 508/248 |
| 5,154,817 | A | 10/1992 | Reid |
| 6,267,791 | B1 | 7/2001 | Thomas et al. |
| 6,607,566 | B1 * | 8/2003 | Coleman et al. ............... 44/301 |
| 2003/0027889 | A1 | 2/2003 | Inhester et al. |
| 2003/0162845 | A1 | 8/2003 | O'Reilly et al. |
| 2003/0209165 | A1 | 11/2003 | Gernon |
| 2010/0242341 | A1 | 9/2010 | Tinetti et al. |

FOREIGN PATENT DOCUMENTS

| JP | 08193015 | 7/1996 |
| WO | 9117746 | 11/1991 |
| WO | 9412028 | 6/1994 |
| WO | 2004057964 | 7/2004 |
| WO | 2006016991 | 2/2006 |
| WO | 2007018782 | 2/2007 |
| WO | 2007032918 | 3/2007 |
| WO | WO 2007018782 A3 * | 4/2007 |
| WO | 2008088632 | 7/2008 |
| WO | 2009140062 | 11/2009 |

OTHER PUBLICATIONS

Noland et al. "JOC 22, 1957,695-697.*
Aitken et al., "Studies on the Condensation Products from N-Primary 1,2-Amino Alcohols and Formaldehyde", Heterocycles, 2004, vol. 64, pp. 277-289.
Borrows et al., "Preparation and Properties, etc: Preparation and Properties of Some Long-Chain Aliphatic Amines", 1947, pp. 197-202, Chapter 47.
Brutto et al., "Some Key Building Blocks for Long-Life Bioresistant Metalworking Fluids", Powerpoint Presentation at STLE Annual Meeting, 2005.
Gernon, "Arkema and Metalworking", Arkema Inc., Tribology & Lubrication Technology 2005, pp. 38-40, vol. 61 No. 11.
Kubis et al., "Investigation on Antibacterial Action of Some Amines", Pharmazie, 1983, pp. 488-489, vol. 38, H. 7.
Macleod et al., "Cation Antagonism of the Antibacterial Action of Amines", Inorganic Ions and Amine Toxicity, 1951, pp. 193-201.
Robbins et al., "A review of the microbiological degradation of fuel", Directory of Microbiocides for the Protection of Materials: A Handbook, 2005, pp. 177-202.
Sandin et al., "The role of alkyl chain length on the antibacterial activity of alkyl ethanolamines", Biomedical Letters, 1992, pp. 85-92, vol. 47, The Faculty Press.
"An Outstanding Multi-functional Amine Additive for Metalworking Fluids", Synergex Premier.
Database WPI Week 199640, Thomson Scientific, London GB; AN 1996-397196 XP002509608 & JP 08193015 abstract.
Database WPI Week 199640 Thomson Scientific, London, GB AN 1996-397196 XP002516784.
"Metalworking Fluid Additives" ANGUS Chemical Company.

* cited by examiner

*Primary Examiner* — Yong Chong
*Assistant Examiner* — Jason A Deck (57) ABSTRACT

Provided are additives of formula I for use in hydrocarbonaceous compositions, such as petroleum or liquid fuels: (I) wherein R1, R2, R3, R4, and R5 are as defined herein. The additives improve the corrosion resistance of the compositions. The additives also enhance the antimicrobial efficacy of any added biocides contained in such compositions.

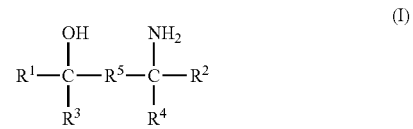

1 Claim, 6 Drawing Sheets

CORROSION AND MICROBIAL CONTROL IN HYDROCARBONACEOUS COMPOSITIONS

CROSS-REFERENCE TO PRIOR RELATED APPLICATIONS

This is a §371 application of PCT International Patent Application Number PCT/US2009/042034 filed Apr. 29, 2009, and claims priority from U.S. Provisional Application No. 61/053,412, filed May 15, 2008, each of which is incorporated herein by reference in its entirety.

FIELD OF THE INVENTION

The invention relates to additives for hydrocarbonaceous compositions. More specifically, the invention relates to aminoalcohol additives that improve the corrosion properties and microbial resistance of hydrocarbonaceous compositions, such as petroleum and fuels. The aminoalcohol additives also enhance the efficacy of biocidal agents typically used in such compositions.

BACKGROUND OF THE INVENTION

Hydrocarbonaceous compositions, such as petroleum (crude oil) and fuels, almost always contain moisture. Additional water can accumulate in tanks as atmospheric moisture condenses. Moisture accumulates in diesel tanks, for example, as condensate droplets on exposed tank surfaces, as dissolved water in the fuel and as water bottoms beneath the fuel. Similarly for petroleum, water can condense and accumulate in pipelines. Alcohol/fuel mixtures, such as "gasohol," tend to absorb and retain higher concentrations of water than does alcohol-free petroleum-based fuel. In addition, more recently, water has begun to be deliberately incorporated into fuel for environmental benefits. It has been found that internal combustion engines, especially diesel engines, that employ water-fuel emulsions can produce lower nitrogen oxides, hydrocarbons and particulate emissions. Reducing emissions from vehicles has been driven by governmental and environmental concerns and so it is expected that the use of aqueous hydrocarbon fuel emulsions will increase.

The presence of water in hydrocarbonaceous compositions, either through deliberate introduction (e.g. emulsified fuel), or through condensation (e.g. in storage or transportation vessels), can, however, lead to problems. Because microbes depend on water for survival, water in the hydrocarbonaceous compositions can cause microbial contamination. Microbes depend on the organic molecules in these compositions for nutrition and growth. Consequently, some species attack the compositions directly, growing at the expense of hydrocarbon and non-hydrocarbon components.

The biodegradation of fuel, in support of microbial growth, is a direct cause of fuel contamination. Color, heat of combustion, pour point, cloud point, thermal stability, detergent and anti-corrosive properties adversely change as microbes selectively attack fuel components. In addition to loss of additive and fuel performance, as bacteria and fungi reproduce, they form biomass, which accumulates at the fuel:water interface, on tank surfaces and on filters. In the case of crude oil, microbiologically influenced corrosion can occur in pipelines as a result of the activity and growth of sulfate reducing bacteria (SRB).

Corrosion issues can also be influenced by the presence of water and acids in hydrocarbonaceous compositions. Biodiesel fuel, in particular, contains free fatty acids and petroleum-derived fuels typically contain residual naphthenic acids and sulfur which can react with water vapor during combustion to form sulfuric acid. While removal of sulfur and acids from fuel is possible, this introduces additional process costs for the fuel manufacturer. In addition, lubricants that are based on phosphoric and carboxylic acids are deliberately added to some fuels (e.g. fuel emulsions) to improve performance. In crude oil, in addition to microbiologically influenced corrosion, the presence of dissolved carbon dioxide (carbonic acid) and/or hydrogen sulfide can also lead to corrosion issues.

In view of the foregoing, a need exists in the art for additives that assist in limiting corrosion and/or microbial growth in hydrocarbonaceous compositions.

BRIEF SUMMARY OF THE INVENTION

The invention provides a blend comprising: a hydrocarbonaceous composition; and a corrosion inhibitory amount of an aminoalcohol of formula (I)

wherein $R^1$, $R^2$, $R^3$, $R^4$, and $R^5$ are as defined below.

The invention also provides a blend comprising a hydrocarbonaceous composition, an aminoalcohol of formula I, and a biocide.

The invention further relates to a method for providing microbial resistance to a biodiesel fuel. The method comprises including in the biodiesel fuel an effective amount of an aminoalcohol of formula I.

DETAILED DESCRIPTION OF THE INVENTION

In one aspect, the invention provides aminoalcohol additives for hydrocarbonaceous compositions. By "hydrocarbonaceous composition" is meant petroleum (crude oil), or liquid fuels such as gasoline, diesel, biodiesel, diesel/biodiesel blends, water-fuel emulsions, ethanol-based fuels, and ether-based fuels. Preferred fuels include those that contain a high level of acid content, such as biodiesels.

The additives inhibit the corrosion of systems in contact with the hydrocarbonaceous compositions, such as storage tanks, pipelines, and engines. The improved corrosion resistance is believed to result, in part, from the ability of the aminoalcohols to control the pH of the compositions.

The additives of the invention are primary aminoalcohol compounds of the formula I:

(I)

wherein:
$R^1$ and $R^3$ are each independently H, linear or branched alkyl, alkenyl, alkynyl, cycloalkyl, or aryl (preferably phenyl), or $R^1$, $R^3$ and the carbon to which they are attached form a cycloalkyl ring, $R^2$ and $R^4$ are each independently H, linear or branched alkyl, cycloalkyl, cycloalkyl-alkyl, aryl, aryl-alkyl, or $R^2$, $R^4$ and the carbon to which they are attached form a cycloalkyl ring; and, provided that $R^2$ and $R^4$ together contain 3 or more carbon atoms; and $R^5$ is absent or is a $C_1$-$C_{10}$ alkylene (bridging alkyl), arylene (preferably phenyl), arylene-alkylene-, or -alkylene-arylene- (e.g., benzyl, phenethyl, and the like);

wherein the alkyl, cycloalkyl, alkylene, aryl, and arylene groups of $R^1$, $R^3$, and $R^5$ are optionally substituted with alkyl or phenyl. The aminoalcohol may be in the form of a mixture of two or more compounds of formula (I).

Preferred aminoalcohols of formula I include compounds of formula I-1, which are compounds of formula I in which $R^1$ is H.

Preferred aminoalcohols of formula I and I-1 include compounds of formula I-2, which are compounds of formula I or I-1 in which $R^2$ is H or linear alkyl.

Preferred aminoalcohols of formulae I, I-1, and I-2 also include compounds of formula I-3, which are compounds of formula I, I-1, or I-2 in which $R^3$ is hydrogen and $R^4$ is linear alkyl.

Preferred aminoalcohols of formulae I, I-1, I-2 and I-3 further include compounds of formula I-4, which are compounds of formula I, I-1, I-2 or I-3 in which $R^5$ is a bond or is a methylene or ethylene bridge.

Further preferred aminoalcohols of formula I include compounds of formula II:

(II)

wherein
$R^2$ and $R^4$ are each independently H, linear or branched alkyl, cycloalkyl, cycloalkyl-alkyl, aryl, aryl-alkyl, or $R^2$, $R^4$ and the carbon to which they are attached form a cycloalkyl ring; and, provided that $R^2$ and $R^4$ together contain 3 or more carbon atoms.

Preferred aminoalcohols of formula (II) include compounds of formula (II-1), which are compounds of formula (II) in which $R^2$ and $R^4$ together contain a total of up to 11 carbon atoms.

Preferred aminoalcohols of formula (II) and formula (II-1) include compounds of formula (II-2), which are compounds of formula (II) or (II-1) in which $R^2$ and $R^4$ are each independently linear alkyl.

Preferred aminoalcohols of formula (II) and formula (II-1) also include compounds of formula (II-3), which are compounds of formula (II) or (II-1) in which one of $R^2$ and $R^4$ is H and the other is linear alkyl.

Preferred aminoalcohols of formula (II) and formula (II-1) include compounds of formula (II-4), which are compounds of formula (II) or (II-1) in which $R^2$ and $R^4$ together with the carbon to which they are attached form a cycloalkyl ring.

Preferred aminoalcohols of formula (II) and formula (II-1) include compounds of formula (II-5), which are compounds of formula (II) or (II-1) in which one of $R^2$ and $R^4$ is $CH_3$ and the other is aryl, preferably phenyl.

Preferred primary amino alcohols for use in the invention include, but are not limited to: 2-amino-2-methyl-1-hexanol, 2-amino-2-ethyl-1-pentanol, 2-amino-2-methyl-1-heptanol, 2-amino-2-ethyl-1-hexanol, 2-amino-2-propyl-1-pentanol, 2-amino-2-methyl-1-octanol, 2-amino-2-ethyl-1-heptanol, 2-amino-2-propyl-1-hexanol, 2-amino-2-methyl-1-nonanol, 2-amino-2-ethyl-1-octanol, 2-amino-2-propyl-1-heptanol, 2-amino-2-butyl-1-hexanol, 2-amino-2-methyl-1-decanol, 2-amino-2-ethyl-1-nonanol, 2-amino-2-propyl-1-octanol, 2-amino-2-butyl-1-heptanol, 2-amino-2-methyl-1-undecanol, 2-amino-2-ethyl-1-decanol, 2-amino-2-propyl-1-nonanol, 2-amino-2-butyl-1-octanol, 2-amino-2-pentyl-1-heptanol, 2-amino-2-methyl-1-dodecanol, 2-amino-2-ethyl-1-undecanol, 2-amino-2-propyl-1-decanol, 2-amino-2-butyl-1-nonanol, 2-amino-2-pentyl-1-octanol, (1-aminocyclopentyl)methanol, (1-aminocyclohexyl)methanol, (1-aminocycloheptyl)methanol, (1-aminocyclooctyl)methanol, (1-aminocyclononyl)methanol, (1-aminocyclodecyl)methanol, (1-aminocycloundecyl)methanol, (1-aminocyclododecyl)methanol, 2-amino-2-phenyl-1-ethanol, 2-amino-2-phenyl-1-propanol, 2-amino-2-phenyl-1-butanol, and mixtures thereof.

Particularly preferred amino alcohols include: 2-amino-2-methyl-1-hexanol, 2-amino-2-ethyl-1-pentanol, 2-amino-2-methyl-1-octanol, 2-amino-2-ethyl-1-heptanol, 2-amino-2-propyl-1-hexanol, (1-aminocyclohexyl)methanol, (1-aminocyclooctyl)methanol, 2-amino-2-phenyl-1-propanol, (1-aminocyclopentyl)methanol, and mixtures thereof.

The amino alcohol compounds may be readily prepared by a person of ordinary skill in the art using techniques well known in the art. For example, such compounds may be prepared by the reaction of nitroalkanes with aliphatic or aromatic aldehydes or ketones or more preferably with formaldehyde, followed by catalytic hydrogenation.

The aminoalcohols may be used in the form of acid salts. Suitable salts include, but are not limited to, boric acid, lactic acid, pelargonic acid, nonanoic acid, neodecanoic acid, sebacic acid, azelaic acid, citric acid, benzoic acid, undecylenic acid, lauric acid, myristic acid, stearic acid, oleic acid, tall oil fatty acid, ethylenediaminetetraacetic acid and like materials. Examples of other salts include linear, branched, cyclic, unsaturated or aromatic mono- or poly-carboxylic acids having 1 to 24 carbons, including formic, acetic, propionic, malic, maleic, benzoic, citric, lactic, 2-ethylhexanoic, lauric, palmitic, oleic, stearic, sebacic, myristic, azelaic, tall oil fatty acids, dimer acids, ethylenediaminetetraacetic acid, and like materials.

The aminoalcohol is generally used in the hydrocarbonaceous composition at a concentration sufficient to provide corrosion stability and/or to increase microbial resistance (in the latter case, when used with biodiesel). The amount required to provide these beneficial effects can be readily determined by a person of ordinary skill in the art. By way of example, it is generally preferred that between about 0.001 and 5 weight percent, more preferably between about 0.001 and 2 weight percent, based on the total weight of the composition, be used.

The aminoalcohol can also be used in combination with other primary, secondary, and tertiary aminoalcohols, as well as with other corrosion inhibitors. The hydrocarbonaceous composition can contain other optional additives. For instance, where the composition is a fuel, typical additives include, without limitation, lubricants, cetane enhancers, combustion promoters, antioxidants/thermal stabilizers, and/or detergents/deposit control additives.

In addition to improved corrosion stability and microbial resistance as described above, it has also been found that the primary aminoalcohols of formula I synergistically enhance the activity of biocides in hydrocarbonaceous compositions. The combination of the aminoalcohol and biocide therefore provides more effective and longer-lasting microbial control at reduced biocide concentrations than would be expected if the biocides were used alone.

Thus, according to a second aspect, the invention provides a blend comprising a hydrocarbonaceous composition, an aminoalcohol of formula I, and a biocide. This aspect of the invention is particularly applicable to compositions that contain water which, as discussed above, is a characteristic of most petroleum and fuels, whether the water is added deliberately (e.g., fuel emulsions) or not. Such compositions typically contain at least 0.01% by weight of water and no more than about 50%.

Preferred hydrocarbonaceous compositions for this second aspect of the invention include petroleum and liquid fuels. Preferred liquid fuels include gasoline, diesel, biodiesel, diesel/biodiesel blends, water-fuel emulsions, ethanol-based fuels, and ether-based fuels. A particularly preferred fuel for this aspect is diesel fuel. As demonstrated by the examples, the aminoalcohols of formula I are themselves non-biocidal in diesel fuel, thus the discovery that they are able to synergistically enhance the efficacy of biocide compounds in diesel in surprising.

Any biocide that is compatible with hydrocarbonaceous compositions may be utilized in the invention. Preferred biocides include: triazines such as 1,3,5-tris-(2-hydroxyethyl)-s-triazine and trimethyl-1,3,5-triazine-1,3,5-triethanol, an example being GROTAN by Troy Corporation, iodopropynylbutylcarbamate, such as POLYPHASE supplied by Troy Corporation, 1,2-benzisothiazolin-3-one, such as BIOBAN BIT marketed by The Dow Chemical Company, 4,4-dimethyloxazolidine, an example being BIOBAN CS-1135 from The Dow Chemical Company, 7-ethyl bicyclooxazolidine, marketed as BIOBAN CS-1246 by The Dow Chemical Co., a combination of 4-(2-nitrobutyl)-morpholine with 4,4'-(2-ethyl-2-nitrotrimethylene)dimorpholine, marketed as FUELSAVER by The Dow Chemical Co., 2-methyl-4-isothiazolin-3-one, a combination of 5-chloro-2-methyl-4-isothiazolin-3-one with 2-methyl-4-isothiazolin-3-one, such as the KATHON brand supplied by Rohm & Haas Corporation, 2-bromo-2-nitro-1,3-propanediol, octylisothiazolinone, dichloro-octylisothiazolinone, dibromo-octylisothiazolinone, phenolics such as o-phenylphenol and p-chloro-m-cresol and their corresponding sodium and/or potassium salts, sodium pyrithione, zinc pyrithione, n-butyl benzisothiazolinone, 1-(3-chloroallyl)-3,5,7-triaza-1-azoniaadamantane chloride, chlorothalonil, carbendazim, diiodomethyltolylsulfone, 2,2-dibromo-3-nitrilopropionamide (DBNPA), glutaraldehyde, N,N'-Methylene-bis-morpholine, ethylenedioxy methanol (e.g. Troyshield B7), phenoxyethanol, (e.g. Comtram 121), tetramethylol acetylenediurea (e.g. Protectol TD), dithiocarbamates, 2,6-Dimethyl-m-dioxan-4-ol acetate (e.g Bioban DXN), dimethylol-dimethyl-hydantoin, tris(hydroxymethyl)nitromethane, bicyclic oxazolidines (e.g. Nuospet 95), (thiocyanomethylthio)-benzothiazole (TCMTB), methylene bis(thiocyanate (MBT), substituted dioxaborinanes such as BIOBOR JF from Hammonds Fuel Additives, tetrakis (hydroxymethyl) phosphonium sulfate (THPS) such as AQUCAR THPS 75 from The Dow Chemical Company, quaternary ammonium compounds such as alkyl dimethyl benzyl ammonium chloride (ADBAC), cocodiamine, dazomet such as Protectol DZ from BASF, and mixtures of two or more thereof.

Further preferred biocides, particularly where the hydrocarbonaceous composition is a liquid fuel, are a combination of 4-(2-nitrobutyl)-morpholine with 4,4'-(2-ethyl-2-nitrotrimethylene)dimorpholine (FUELSAVER from The Dow Chemical Company), a combination of 5-chloro-2-methyl-4-isothiazolin-3-one with 2-methyl-4-isothiazolin-3-one (CMIT/MIT), a combination of (thiocyanomethylthio)-benzothiazole (TCMTB) and methylene bis(thiocyanate (MBT), substituted dioxaborinanes, oxazolidines such as 4,4-dimethyloxazolidine and 7-ethyl bicyclooxazolidine, and mixtures of two or more thereof.

Further preferred biocides for petroleum include glutaraldehyde, 2-bromo-2-nitro-1,3-propanediol, isothiazolinones such as BIT and CMIT/MIT, 2,2-dibromo-3-nitrilopropionamide (DBNPA), tetrakis(hydroxymethyl) phosphonium sulfate (THPS), oxazolidines such as 4,4-dimethyloxazolidine and 7-ethyl bicyclooxazolidine, quaternary ammonium compounds such as alkyl dimethyl benzyl ammonium chloride (ADBAC), cocodiamine, dazomet, and mixtures of two or more thereof.

In the invention, the biocide (or combination of biocides) is preferably present in the blend at a concentration of between about 0.001 and 2 weight percent based on the total weight of the blend. However, in order to reduce cost and minimize potential for adverse environmental impact, it is preferred that low concentrations of biocides be used. Indeed, it is one of the advantages of the invention that by enhancing the efficacy of the biocide, the aminoalcohols described herein permit less biocide to be used than could be achieved without the aminoalcohol.

The concentration of aminoalcohol of formula I relative to biocide in the blend is not critical, but in some preferred embodiments corresponds to a weight ratio of aminoalcohol to biocide between about 5000:1 and about 1:2. In further preferred embodiments, the weight ratio of aminoalcohol to biocide is between about 100:1 and 1:2. In still further preferred embodiments, the weight ratio is between about 60:1 and 1:1.

A preferred fuel blend according to the invention comprises:
  (a) a liquid fuel;
  (b) an aminoalcohol of formula (I) as defined above: and
  (c) a biocide selected from the group consisting of:
    (i) a blend of 4-(2-nitrobutyl)-morpholine with 4,4'-(2-ethyl-2-nitrotrimethylene)dimorpholine (FUELSAVER from The Dow Chemical Company);
    (ii) a blend of 5-chloro-2-methyl-4-isothiazolin-3-one with 2-methyl-4-isothiazolin-3-one;

(iii) a blend of (thiocyanomethylthio)-benzothiazole (TC-MTB) and methylene bis(thiocyanate (MBT);
(iv) a substituted dioxaborinane; and
(v) an oxazolidine.

In this embodiment, the weight ratio of aminoalcohol to biocide (i) is preferably between about 30:1 and 1:1, more preferably between about 25:1 and 1.5:1. Further, the weight ratio of aminoalcohol to biocide (ii) is preferably between about 70:1 and 3:1.

A more preferred fuel blend according to the invention comprises:
(a) a liquid fuel;
(b) an aminoalcohol of formula II as defined above; and
(c) a biocide selected from the group consisting of:
(i) a blend of 4-(2-nitrobutyl)-morpholine with 4,4'-(2-ethyl-2-nitrotrimethylene) dimorpholine;
(ii) a blend of 5-chloro-2-methyl-4-isothiazolin-3-one with 2-methyl-4-isothiazolin-3-one;
(iii) a blend of (thiocyanomethylthio)-benzothiazole and methylene bis(thiocyanate);
(iv) a substituted dioxaborinane; and
(v) an oxazolidine.

In this embodiment, the weight ratio of aminoalcohol to biocide (i) is preferably between about 30:1 and 1:1, more preferably between about 25:1 and 1.5:1. Further, the weight ratio of aminoalcohol to biocide (ii) is preferably between about 70:1 and 3:1.

A preferred petroleum based blend according to the invention comprises:
(a) petroleum;
(b) an aminoalcohol of formula (I) as defined above: and
(c) a biocide selected from the group consisting of: glutaraldehyde, 2-bromo-2-nitro-1,3-propanediol, tetrakis(hydroxymethyl) phosphonium sulphate (THPS), 2,2-dibromo-3-nitrilopropionamide (DBNPA), an isothiazolinone compound, a quaternary ammonium compound, cocodiamine; and, dazomet.

A more preferred petroleum blend according to the invention comprises:
(a) petroleum;
(b) an aminoalcohol of formula II as defined above; and
(c) a biocide selected from the group consisting of: glutaraldehyde, 2-bromo-2-nitro-1,3-propanediol, tetrakis(hydroxymethyl) phosphonium sulphate (THPS), 2,2-dibromo-3-nitrilopropionamide (DBNPA), an isothiazolinone compound, quaternary ammonium compounds, cocodiamine, and dazomet.

"Alkyl," as used in this specification, encompasses straight and branched chain aliphatic groups having from 1-8 carbon atoms, more preferably 1-6 carbon atoms. Preferred alkyl groups include, without limitation, methyl, ethyl, propyl, isopropyl, butyl, isobutyl, sec-butyl, tert-butyl, pentyl, hexyl, heptyl, octyl, nonyl, decyl, and undecyl.

The term "alkenyl" as used herein means an unsaturated straight or branched chain aliphatic group with one or more carbon-carbon double bonds, having from 2-8 carbon atoms, and preferably 2-6 carbon atoms. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2-8 carbon atoms, and preferably 2-6 carbon atoms. Preferred alkynyl groups include, without limitation, ethynyl, propynyl, butynyl, pentynyl, and hexynyl.

An "alkylene" group is an alkyl as defined hereinabove, that is positioned between and serves to connect two other chemical groups. Preferred alkylene groups include, without limitation, methylene, ethylene, propylene, and butylene.

The term "cycloalkyl" as employed herein includes saturated and partially unsaturated cyclic hydrocarbon groups having 3 to 12 carbons, preferably 3 to 8 carbons. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a C6-C12 aromatic moiety comprising one to three aromatic rings. Preferably, the aryl group is a C6-C10 aryl group. Preferred aryl groups include, without limitation, phenyl, naphthyl, anthracenyl, and fluorenyl. More preferred is phenyl.

Alkyl, cycloalkyl, and aryl (and their bridging derivatives alkylene, cycloalkylene, and arylene) are optionally substituted with one or more other alkyl (e.g., methyl, ethyl, butyl), phenyl, or both.

Unless otherwise indicated, ratios, percentages, parts, and the like used herein are by weight.

The following examples are illustrative of the invention but are not intended to limit its scope.

EXAMPLES

Example 1

Preparation of 1-aminocyclohexylmethanol.
(ACyHM)

A 2-liter 3-neck flask equipped with a magnetic stirrer, nitrogen blanket, thermocouple controlled heating mantle and addition funnel is charged with nitrocyclohexane (521 g, 4.04 mol). Triethylamine catalyst (10.0 mL) is added and the yellow mixture warmed to 55° C. using the heating mantle. Via the addition funnel, aqueous formaldehyde (37% wt., 330 mL, 4.4 mol) is added dropwise over the period of 90 minutes. The reaction is very mildly exothermic, warming to 60° C. during the addition. After all the formaldehyde has been added, the reaction mixture is held at 60° C. for an additional 2 hours, poured into a separatory funnel and allowed to cool/phase separate overnight. The bottom, orange product layer is collected (750.8 g, contains dissolved water) and GC analysis indicates 96.9% purity with approximately 1.7% nitrocyclohexane and 1.4% triethylamine. The product is used without further purification.

Catalytic hydrogenation of the 1-nitrocyclohexylmethanol to the 1-aminocyclohexylmethanol. A 2-liter Parr autoclave is charged with methanol (310 mL) and Raney Nickel catalyst (R-3111, 43.7 g wet weight). The reactor is sealed, purged with nitrogen followed by purging with hydrogen and then brought up to 65° C. under 500 psi hydrogen pressure. With rapid stiffing, a solution of 1-nitrocyclohexylmethanol (4.04 mol actives containing about 105 g water) in methanol (800 mL total solution) is added over 3 hours while maintaining 65° C./500 psi hydrogen. When the addition is completed, the reaction is allowed to continue for an additional 20 minutes followed by cooling to room temperature. The autoclave is vented, opened and the crude product isolated via vacuum filtration. The methanol solvent is removed on a rotary evaporator at 50° C./29" vacuum. The yield of crude, stripped product is 755.6 g (still contains water). This is vacuum distilled through a fractionating column packed with stainless steel mesh, the product boiling between 85-86° C./15 ton is collected. GC analysis indicates >97% purity for the water white oil. The oil slowly crystallizes on standing. A final yield of 88% (459 g) of the purified product is obtained.

Example 2

Preparation of Mixture of 2-Amino-2-methyl-1-octanol, 2-Amino-2-ethyl-1-heptanol, and 2-Amino-2-propyl-1-hexanol (collectively "AoctM")

Using the above procedure, a mixture of 2-amino-2-methyl-1-octanol, 2-amino-2-ethyl-1-heptanol, and 2-amino-2-propyl-1-hexanol is prepared from a mixture of 2-nitrooctane, 3-nitrooctane and 4-nitrooctane. This mixture of amino alcohols is used in the testing.

Examples 3-26

Corrosion Testing

Examples 3-26 illustrate the effect of the aminoalcohols of the invention on the corrosion of metals in contact with fuels.

Mild carbon steel (MCS), low carbon fine grain steel (LCFGS) and cast iron (CI) coupons from Metaspec Co are used. Each coupon measures 1"×2"×⅛". All coupons are cleaned with acetone prior to total immersion in diesel or biodiesel fuel. Each coupon is weighed before testing and again after testing and cleaning. Fuels and water are placed into 4 oz wide-mouth flint glass jars and one coupon is totally submerged in the fuel in each jar. The test system consists of 80% fuel and 20% deionized water (weight basis). For test samples, the aminoalcohol is added at 0.427% on the total weight of fuel plus water (56 grams of fuel+14 grams of DI water+0.30 grams aminoalcohol). Samples are heated at 50° C. in a mechanical convection oven. The coupons are checked visually each week, and the fuel color is noted. Jars are agitated to disperse the water and rotated to view coupons in the fuel; the weekly agitation simulates agitation due to periodic fuel addition and withdrawal from storage tanks. The jars remain closed during the testing. After the testing, the coupons are re-weighed and visually assessed for corrosion. Results for the inventive amino alcohols are represented in Tables 1-2.

As can be seen in Tables 1-2, the amino alcohols of the invention reduce mass loss for all metals tested in contact with the diesel fuel/water mixtures. In addition, visual corrosion is eliminated with all metals. For biodiesel fuel, a reduction in weight loss is not observed, however, a visual reduction in corrosion is observed for AOctM with cast iron.

TABLE 1

Corrosion testing results for AOctM

| Ex. No. | Metal | Fuel | Biocide | Wt Before (g) | Wt After (g) | Wt Loss (g) | Corrosion (visual) |
|---|---|---|---|---|---|---|---|
| 3 | MCS | Diesel | AOctM | 8.2864 | 8.2861 | −0.0003 | No |
| 4 | MCS | Diesel | None (control) | 8.2285 | 8.2153 | −0.0132 | Yes |
| 5 | MCS | Biodiesel | AOctM | 8.2655 | 8.2600 | −0.0055 | No |
| 6 | MCS | Biodiesel | None (control) | 8.2526 | 8.2506 | −0.0020 | No |
| 7 | LCFGS | Diesel | AOctM | 28.1307 | 28.1303 | −0.0004 | No |
| 8 | LCFGS | Diesel | None (control) | 26.1902 | 26.1634 | −0.0268 | Yes |
| 9 | LCFGS | Biodiesel | AOctM | 27.1069 | 27.0932 | −0.0137 | No |
| 10 | LCFGS | Biodiesel | None (control) | 25.7571 | 25.7538 | −0.0033 | No |
| 11 | CI | Diesel | AOctM | 29.2198 | 29.2251 | 0.0053 | No |
| 12 | CI | Diesel | None (control) | 28.7833 | 28.7576 | −0.0257 | Yes |
| 13 | CI | Biodiesel | AOctM | 30.3194 | 30.2298 | −0.0896 | No |
| 14 | CI | Biodiesel | None (control) | 28.8358 | 28.8406 | 0.0048 | Yes |

MCS = Mild Carbon Steel; LCFGS = Low Carbon Fine Grain Steel; CI = cast iron. AOctM = Mixture of 2-Amino-2-methyl-1-octanol, 2-Amino-2-ethyl-1-heptanol, and 2-Amino-2-propyl-1-hexanol

TABLE 2

Corrosion testing results for ACyHM

| Ex. No. | Metal | Fuel | Biocide | Wt Before (g) | Wt After (g) | Wt Loss (g) | Corrosion (visual) |
|---|---|---|---|---|---|---|---|
| 15 | MCS | Diesel | ACyHM | 8.2846 | 8.2843 | −0.0003 | Yes |
| 16 | MCS | Diesel | None (control) | 8.2540 | 8.2326 | −0.0214 | Yes |
| 17 | MCS | Biodiesel | ACyHM | 8.2744 | 8.2644 | −0.0100 | No |
| 18 | MCS | Biodiesel | None (control) | 8.1942 | 8.1921 | −0.0021 | No |
| 19 | LCFGS | Diesel | ACyHM | 31.4037 | 28.9904 | −0.0007 | No |
| 20 | LCFGS | Diesel | None (control) | 29.0032 | 27.5521 | −0.0275 | Yes |
| 21 | LCFGS | Biodiesel | ACyHM | 28.4691 | 26.9273 | −0.0059 | No |
| 22 | LCFGS | Biodiesel | None (control) | 27.8876 | 28.5168 | −0.0034 | No |
| 23 | CI | Diesel | ACyHM | 28.9848 | 28.9889 | 0.0041 | No |
| 24 | CI | Diesel | None (control) | 27.5733 | 27.5521 | −0.0212 | Yes |
| 25 | CI | Biodiesel | ACyHM | 26.9380 | 26.9273 | −0.0107 | No |
| 26 | CI | Biodiesel | None (control) | 28.5250 | 28.5618 | −0.0082 | No |

MCS = Mild Carbon Steel; LCFGS = Low Carbon Fine Grain Steel; CI = cast iron. ACyHM = 1-aminocyclohexylmethanol.

Microbial Resistance Examples

The following examples illustrate the effect of the aminoalcohols on the microbial resistance of fuels with and without biocides.

Materials

Bacteria:

Pseudomonas aeruginosa ATCC#33988, Yeast: *Yarrowia tropicalis* ATCC#48138, and Mold: *Hormoconis resinae* ATCC#20495, are sub cultured in Bushnell-Haas broth, and used for the mixed inoculum. The organism concentrations in the mixed inoculum are as follows: *Ps. aeruginosa*-5.2×10$^8$ cfu/mL; *Y. tropicalis*-4.6×10$^7$ cfu/mL; *H. resinae*-4.2×10$^7$ cfu/mL These bacteria are organisms commonly used in microbial testing of fuels.

Diesel Fuel.

2007 Certification Diesel, Batch #WA1421LT10, is obtained from Halternann Products (a subsidiary of The Dow Chemical Company), Channelview, Tex. Product Number: HF 0582.

Biodiesel Fuel.

Biodiesel for these examples is obtained from Stepan Company (Northfield, Ill.) as SB-W.

Biocide.

The biocide chosen for this evaluation is FUELSAVER™ ("FS") from The Dow Chemical Company which is a combination of 4-(2-nitrobutyl)-morpholine with 4,4'-(2-ethyl-2-nitrotrimethylene)dimorpholine.

Biocide (FUELSAVER™) Loading.

135 and 1000 ppm.

Amino Alcohols Tested.

2-amino-2-methyl-1-propanol (AMP) (Comparative Example), ACyHM (Example A), and AOctM (Example B), triethanolamine (TEA) (Comparative Example).

Amino Alcohol Salts Tested.

Salt of AOctM and oleic acid, Salt of AOctM and acetic acid, Salt of TEA and oleic acid (Comparative Example). Salts of liquid amino alcohols and liquid carboxylic acids are prepared by weighing equimolar amounts of each and mixing them well until homogeneous. For amino alcohols and/or carboxylic acids that are solid, the salts are prepared by mixing equimolar amounts in methanol, mixing until homogeneous, and then stripping off the solvent.

Oleic Acid and Potassium Oleate.

The oleic acid is obtained from Aldrich. The potassium oleate is prepared from oleic acid and potassium hydroxide in the same fashion as the amino alcohol salts above.

Amino Alcohol Loading.

The amino alcohols are evaluated in diesel and biodiesel with and without biocides at one or more of the following loadings: 100, 500, 1500 and 3000 ppm.

Amino Alcohol Salt, Oleic Acid, and Potassium Oleate Loadings.

The amino alcohol salts, oleic acid, and potassium oleate are evaluated in biodiesel at one or more of the following loadings: 100, 500, and 1500 ppm Microbial Testing Procedures Testing is carried out in glass bottles with bakelite screw tops for a minimum of four weeks. For each fuel sample, the aminoalcohol and then the biocide when present are added at the desired loadings to 130 mL of diesel fuel with agitation for 5 min Bushnell-Haas broth (24 mL) is added as the aqueous phase below the diesel fuel. One mL of the mixed inoculum is added. The samples are mixed weekly by turning the bottle upside down 5 times. The organism count listed for day 0 represents the initial organism populations detected in the water bottom after mixing the water bottom and the fuel.

Microbial survival is measured using the plate count method. Tryptic soy agar is used for *Pseudomonas aeruginosa*, and Sabouraud dextrose agar with 0.5 ug/ml gentamycin for *Yarrowia tropicalis*, and bacteriological grade agar 1.5%, with 0.01% potassium tellurite for *Hormoconis resinae*. Bacteria are incubated at 37° C. for 48 hours, and fungi at 25° C. for 5-7 days.

Figure 1:
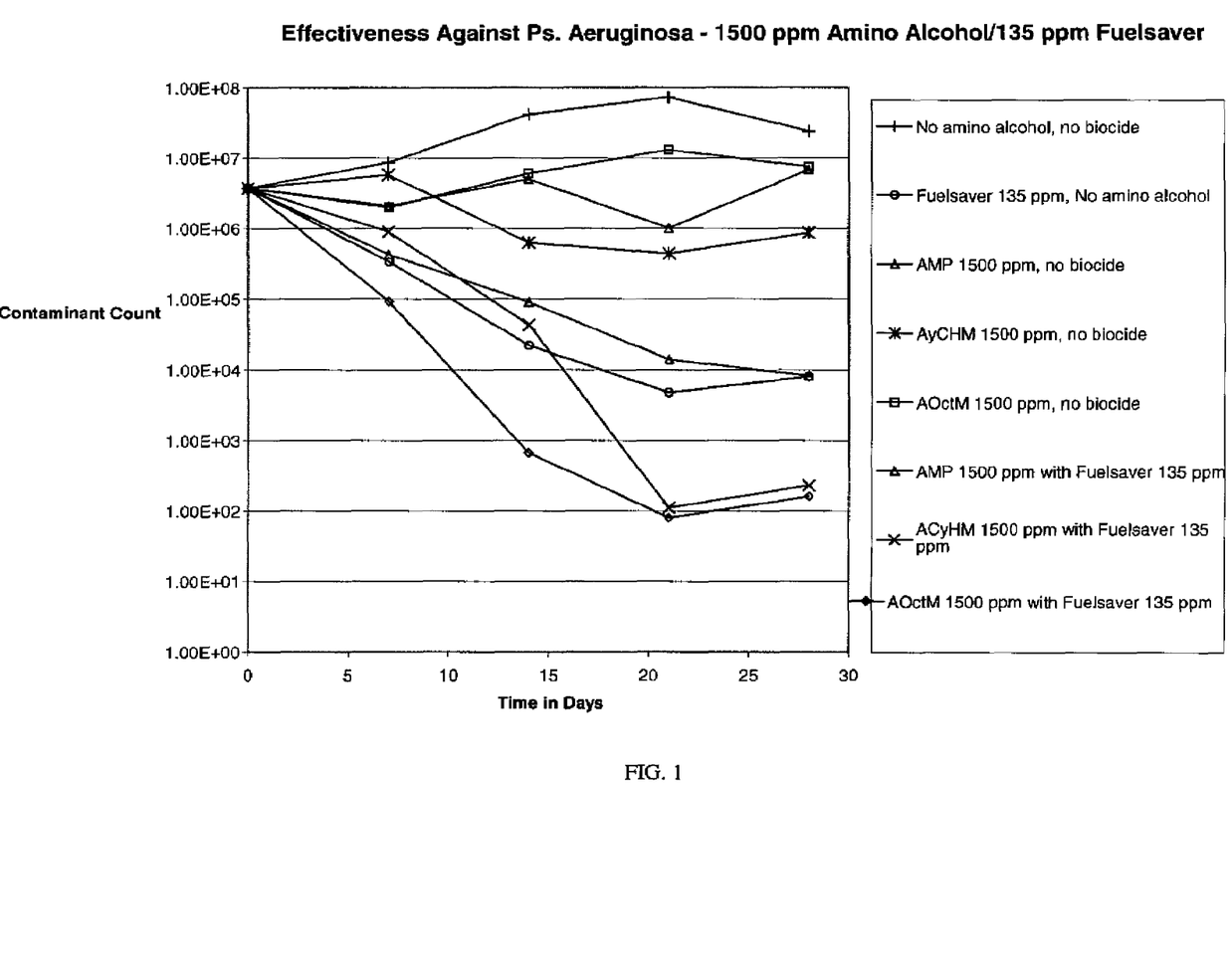
FIG. 1 is a chart comparing the effectiveness of various amino alcohol compounds at a 1500 ppm concentration together with biocide (at 135 ppm concentration) against *Ps. Aeruginosa* in a diesel fuel.
Figure 2:
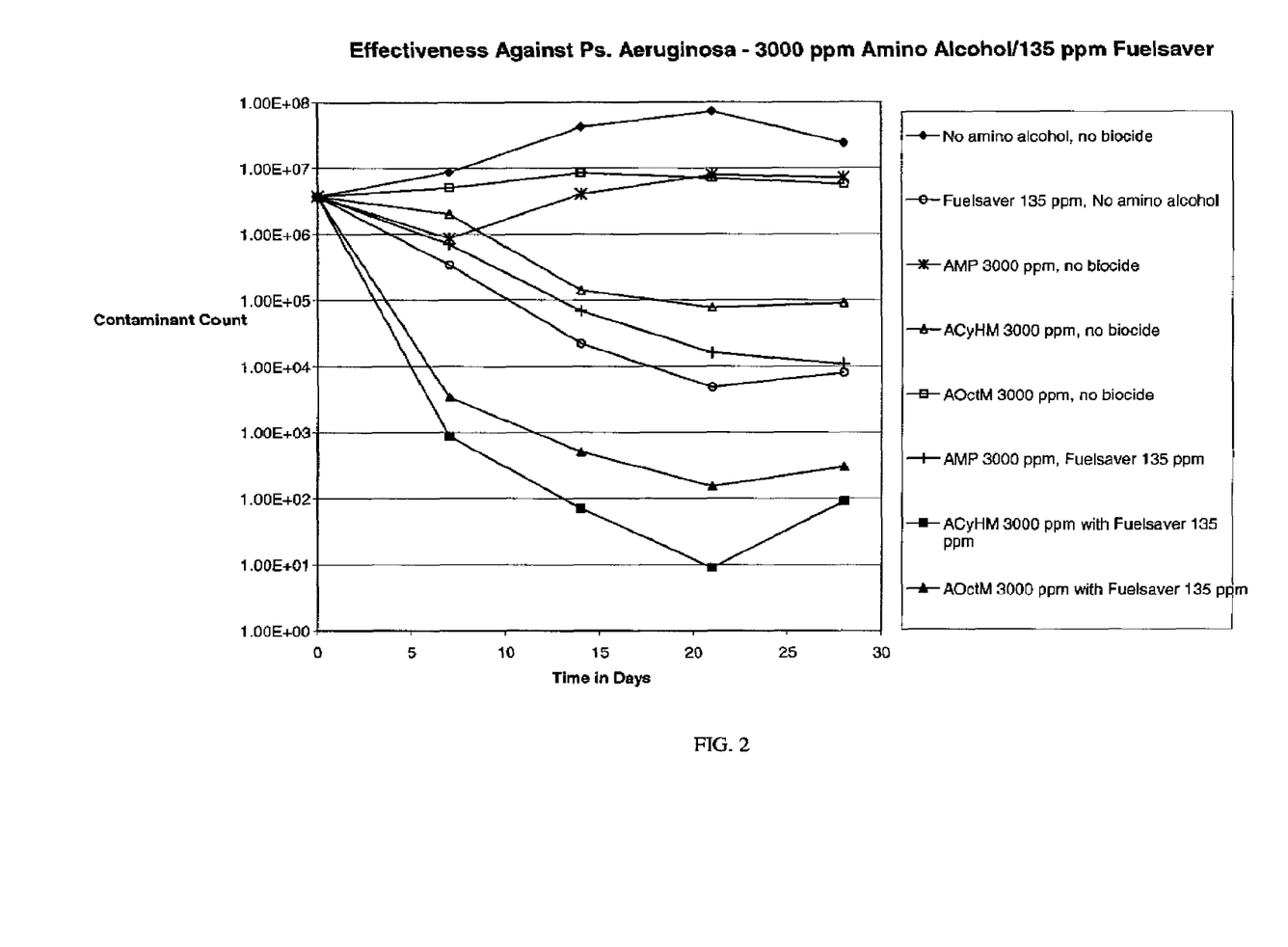
FIG. 2 is a chart comparing the effectiveness of various amino alcohol compounds at a 3000 ppm concentration together with biocide (at 135 ppm concentration) against *Ps. Aeruginosa* in a diesel fuel.
Figure 3:
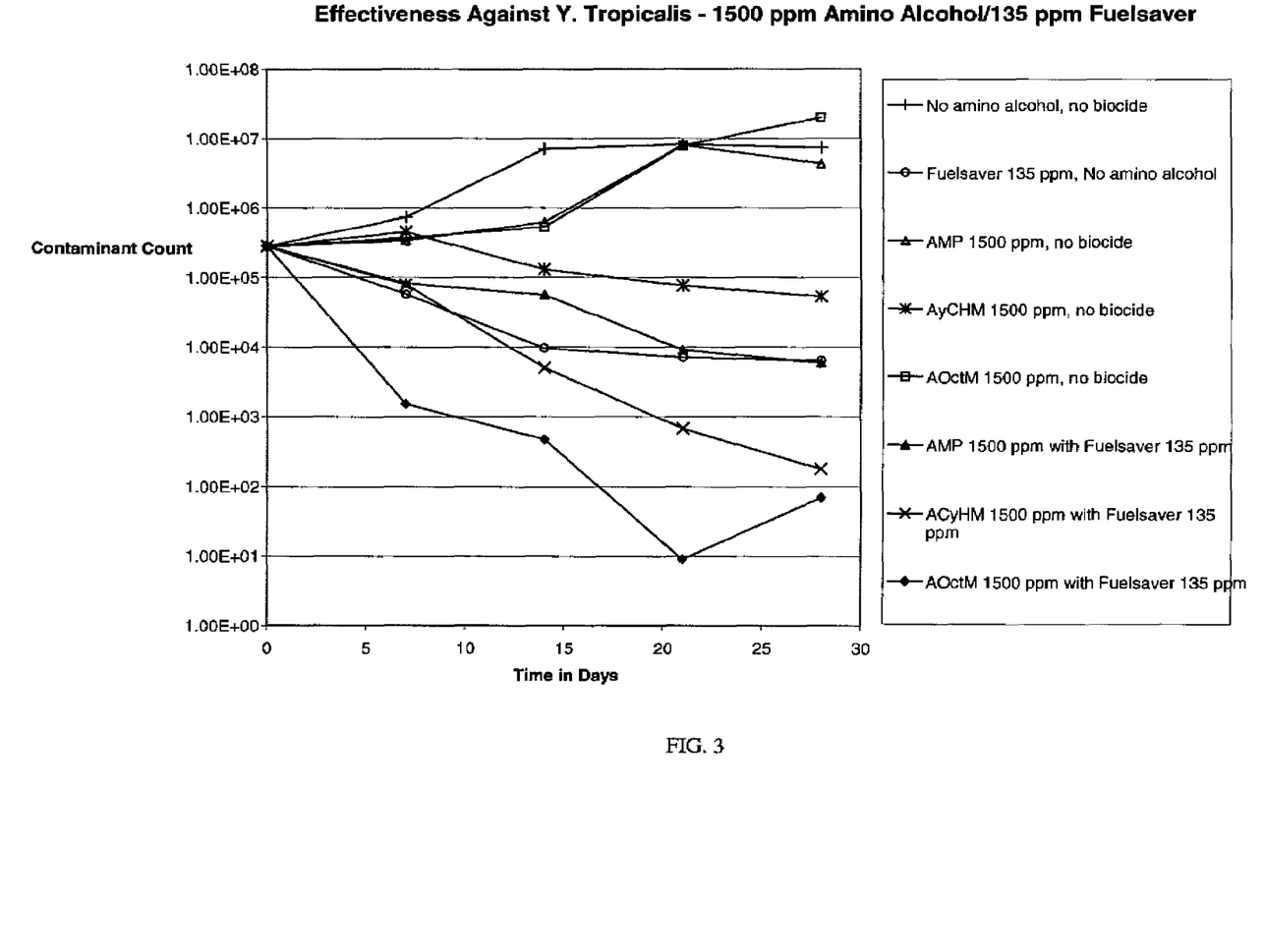
FIG. 3 is a chart comparing the effectiveness of various amino alcohol compounds at a 1500 ppm concentration together with biocide (at 135 ppm concentration) against *Y. Tropicalis* in a diesel fuel.
Figure 4:
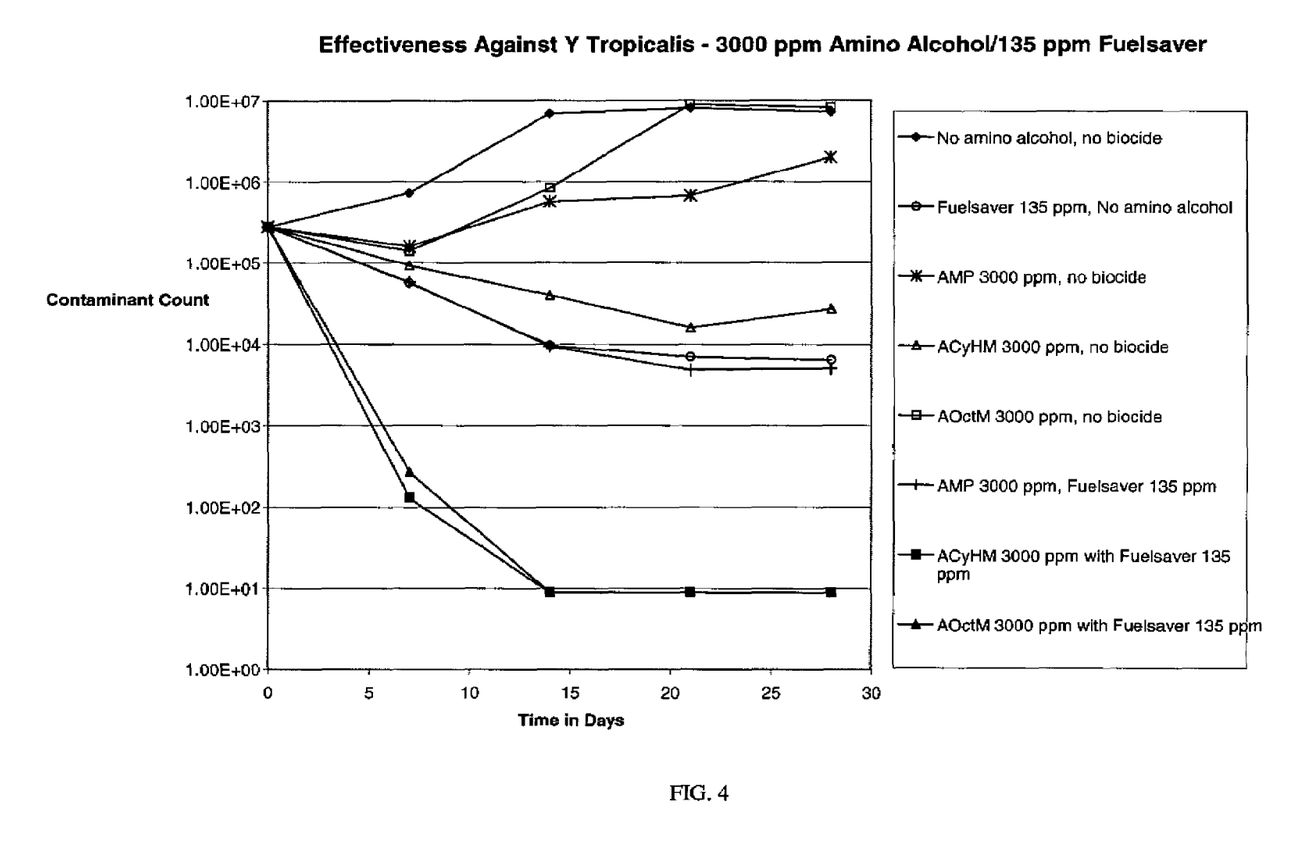
FIG. 4 is a chart comparing the effectiveness of various amino alcohol compounds at a 3000 ppm concentration together with biocide (at 135 ppm concentration) against *Y. Tropicalis* in a diesel fuel.
Figure 5:
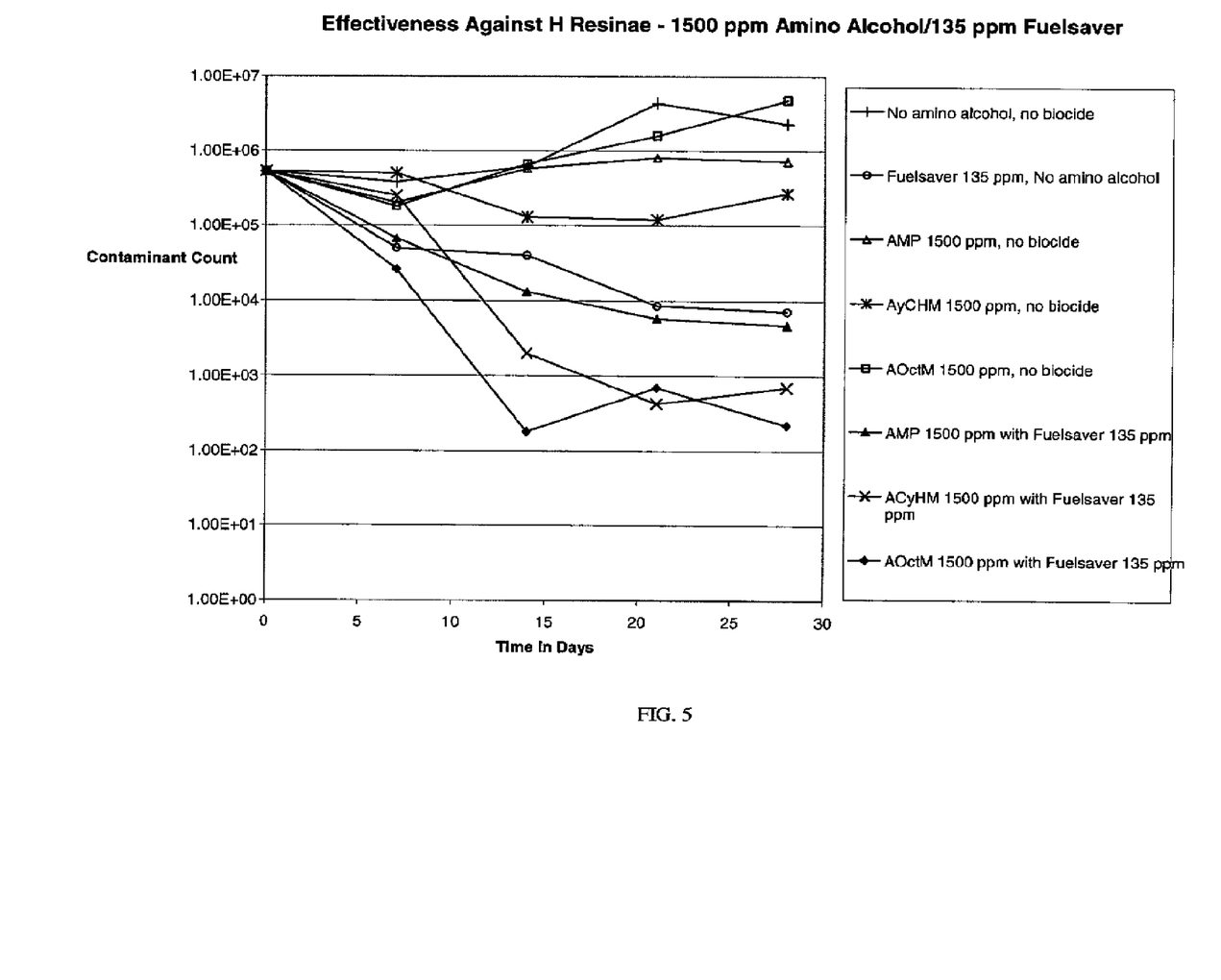
FIG. 5 is a chart comparing the effectiveness of various amino alcohol compounds at a 1500 ppm concentration together with biocide (at 135 ppm concentration) against *H. Resinae* in a diesel fuel.
Figure 6:
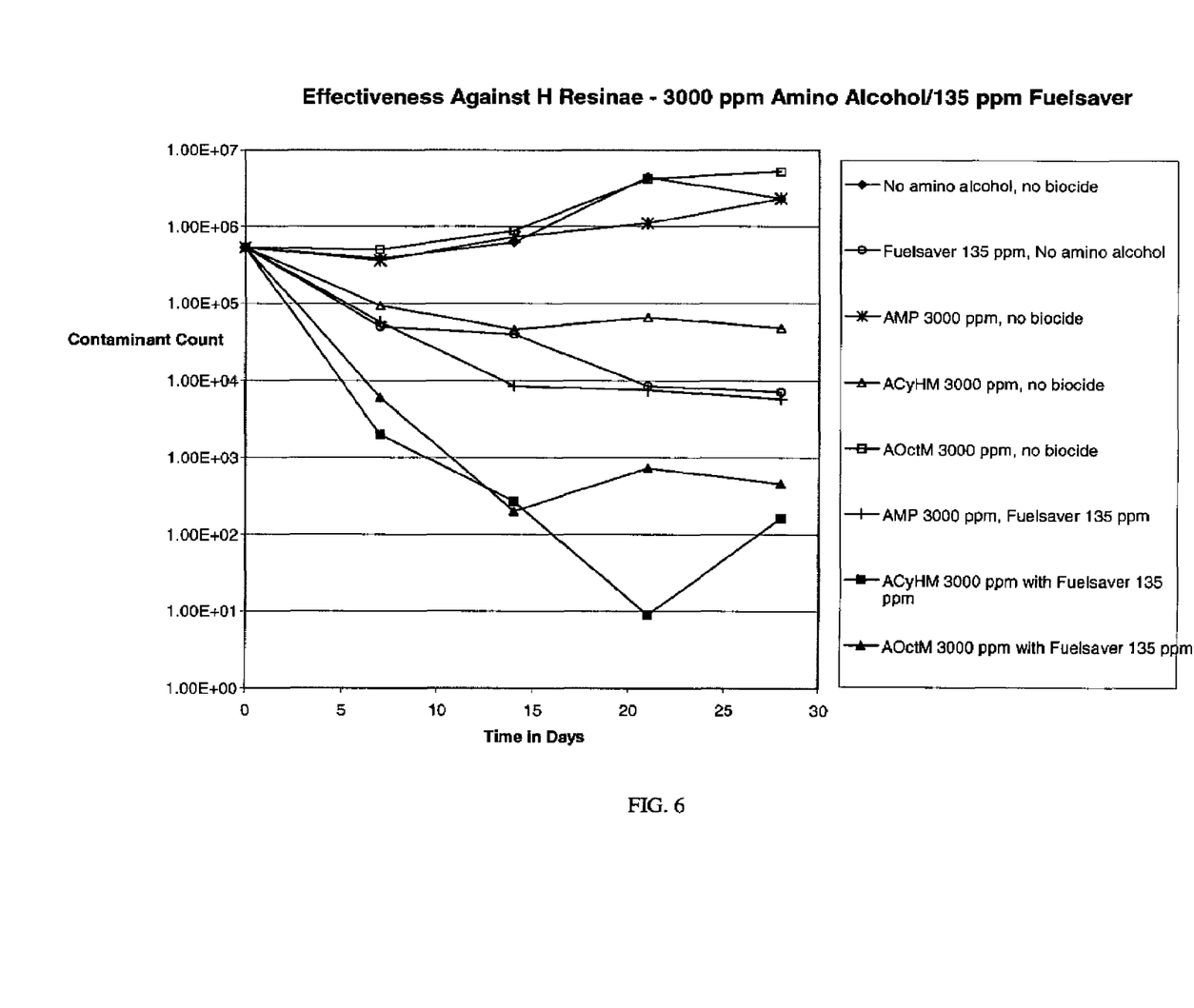
FIG. 6 is a chart comparing the effectiveness of various amino alcohol compounds at a 3000 ppm concentration together with biocide (at 135 ppm concentration) against *H. Resinae* in a diesel fuel.

The data collected from the evaluation of the aminoalcohols in diesel fuel is represented by Tables 3-13 and FIGS. 1-6. Note: The plotted graphs illustrate the enhancement achieved at 135 ppm FUELSAVER. Where a <10 organism count is observed, "9" is used for graphing purposes. As can be seen from the data, in diesel fuel none of the aminoalcohols are able to increase the microbial resistance of the fuel by themselves. Synergy, however, is observed between the amino alcohols of the invention and biocide. The synergy is most apparent at low loadings of biocide, because at the high loadings, the biocides themselves are essentially completely effective over the time period tested.

The data collected from the evaluation of the aminoalcohols of the invention in biodiesel fuel is represented by Tables 14-17. As can be seen from the data, the presence of aminoalcohol in biodiesel enhances the microbial resistance of biodiesel even in the absence of biocide.

The data collected from the evaluation of preformed aminoalcohol salts of the invention in biodiesel fuel (in the absence of biocide) is represented by Table 15-17. As can be seen, like AOctM itself, the addition of the preformed salt of AOctM and oleic acid significantly enhances the microbial resistance of biodiesel even in the absence of biocide. The salt of AOctM and acetic acid is not as effective, though some inhibition against bacteria is achieved at higher loadings. A comparison of AOctM with AOctM oleate, oleic acid, and potassium oleate indicates that certain salts of the inventive aminoalcohols are more effective than the aminoalcohols themselves. For example, AOctM oleate at 1500 ppm, contains about 36% by weight AOctM (540 ppm), and is completely inhibitory for 12 weeks. AOctM at 500 ppm however, shows inhibitory effects for only 2-4 weeks that diminish thereafter. As oleic acid and potassium oleate have no effect at these levels, it appears that AOctM oleate is more effective relative to AOctM.

TABLE 3

Microbial test results for diesel fuel with AOctM

|  | 1. AOctM 1500 ppm | | | 2. AOctM liquid 3000 ppm | | |
| --- | --- | --- | --- | --- | --- | --- |
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 2.0E6 | 3.7E5 | 1.8E5 | 5.0E6 | 1.4E5 | 5.0E5 |
| Wk 2 | 6.0E6 | 5.3E5 | 6.7E5 | 8.4E6 | 8.4E5 | 8.8E5 |

TABLE 3-continued

Microbial test results for diesel fuel with AOctM

| | 1. AOctM 1500 ppm | | | 2. AOctM liquid 3000 ppm | | |
|---|---|---|---|---|---|---|
| Time | Ps. aeruginosa | Y. tropicalis | H. resinae | Ps. aeruginosa | Y. tropicalis | H. resinae |
| Wk 3 | 1.3E7 | 7.8E6 | 1.6E6 | 7.0E6 | 9.0E6 | 4.2E6 |
| Wk 4 | 7.5E6 | 2.0E7 | 4.8E6 | 5.7E6 | 8.3E6 | 5.2E6 |

TABLE 4

Microbial test results for diesel fuel with AOctM
(1500 ppm) and biocide (FUELSAVER ™)

| | 3. AOctM 1500 ppm/FS 135 ppm | | | 4. AOctM 1500 ppm/FS 1000 ppm | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 9.3E4 | 1.5E3 | 2.6E4 | 1.3E2 | 5.0E2 | 8.7E2 |
| Wk 2 | 6.7E2 | 4.7E2 | 1.8E2 | 7.0E1 | <10 | 9.0E1 |
| Wk 3 | 8.0E1 | <10 | 7.0E2 | <10 | <10 | <10 |
| Wk 4 | 1.6E2 | 7.0E1 | 2.2E2 | <10 | <10 | <10 |

TABLE 5

Microbial test results for diesel fuel with AOctM
(3000 ppm) and biocide (FUELSAVER ™)

| | 5. AOctM 3000 ppm/FS 135 ppm | | | 6. AOctM 3000 ppm/FS 1000 ppm | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 3.4E3 | 2.7E2 | 6.1E3 | <10 | 3.7E2 | 2.0E3 |
| Wk 2 | 5.0E2 | <10 | 2.0E2 | <10 | <10 | <10 |
| Wk 3 | 1.5E2 | <10 | 7.3E2 | <10 | <10 | <10 |
| Wk 4 | 3.0E2 | <10 | 4.6E2 | <10 | <10 | <10 |

TABLE 6

Microbial test results for diesel fuel with ACyHM

| | 7. ACyHM solid 1500 ppm | | | 8. ACyHM 3000 ppm | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 5.8E6 | 4.5E5 | 5.0E5 | 2.0E6 | 9.3E4 | 9.4E4 |
| Wk 2 | 6.3E5 | 1.3E5 | 1.3E5 | 1.4E5 | 4.0E4 | 4.6E4 |
| Wk 3 | 4.4E5 | 7.6E4 | 1.2E5 | 7.7E4 | 1.6E4 | 6.6E4 |
| Wk 4 | 8.7E5 | 5.3E4 | 2.7E5 | 9.0E4 | 2.7E4 | 4.8E4 |

TABLE 7

Microbial test results for diesel fuel with ACyHM
(1500 ppm) and biocide (FUELSAVER ™)

| | 9. ACyHM 1500 ppm/FS 135 ppm | | | 10. ACyHM 1500 ppm/FS 1000 ppm | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 9.0E5 | 7.8E4 | 2.5E5 | 7.8E3 | 1.6E4 | 1.1E4 |
| Wk 2 | 4.3E4 | 5.0E3 | 2.0E3 | <10 | <10 | <10 |
| Wk 3 | 1.1E2 | 6.7E2 | 4.3E2 | <10 | <10 | <10 |
| Wk 4 | 2.3E2 | 1.8E2 | 7.0E2 | <10 | <10 | 8.0E1 |

TABLE 8

Microbial test results for diesel fuel with ACyHM (3000 ppm) and biocide (FUELSAVER ™)

| | 11. ACyHM 3000 ppm/FS 135 ppm | | | 12. ACyHM 3000 ppm/FS 1000 ppm | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 8.6E2 | 1.3E2 | 2.0E3 | <10 | <10 | 4.3E2 |
| Wk 2 | 7.0E1 | <10 | 2.7E2 | <10 | <10 | <10 |
| Wk 3 | <10 | <10 | <10 | <10 | <10 | 5.0E1 |
| Wk 4 | 9.0E1 | <10 | 1.6E2 | <10 | <10 | <10 |

TABLE 9

Microbial test results for diesel fuel with AMP

| | 13. AMP 1500 ppm (Comparative) | | | 14. AMP 3000 ppm (Comparative) | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 2.1E6 | 3.4E5 | 2.0E5 | 8.6E5 | 1.6E5 | 3.6E5 |
| Wk 2 | 5.0E6 | 6.2E5 | 5.8E5 | 4.0E6 | 5.7E5 | 7.3E5 |
| Wk 3 | 1.0E6 | 8.0E6 | 8.1E5 | 7.8E6 | 6.8E5 | 1.1E6 |
| Wk 4 | 6.8E6 | 4.3E6 | 7.2E5 | 7.2E6 | 2.0E6 | 2.3E6 |

TABLE 10

Microbial test results for diesel fuel with AMP (1500 ppm) and biocide (FUELSAVER ™)

| | 15. AMP 1500 ppm/FS 135 ppm (Comparative) | | | 16. AMP 1500 ppm/FS 1000 ppm (Comparative) | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 4.3E5 | 8.2E4 | 6.7E4 | 1.4E2 | 5.2E2 | 9.2E2 |
| Wk 2 | 9.0E4 | 5.6E4 | 1.3E4 | <10 | <10 | <10 |
| Wk 3 | 1.4E4 | 9.0E3 | 5.8E3 | <10 | <10 | <10 |
| Wk 4 | 8.2E3 | 5.9E3 | 4.7E3 | <10 | <10 | <10 |

TABLE 11

Microbial test results for diesel fuel with AMP (3000 ppm) and biocide (FUELSAVER ™)

| | 17. AMP 3000 ppm/FS 135 ppm (Comparative) | | | 18. AMP 3000 ppm/FS 1000 ppm (Comparative) | | |
|---|---|---|---|---|---|---|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 7.0E5 | 5.8E4 | 5.7E4 | <10 | 9.4E2 | 7.0E3 |
| Wk 2 | 6.8E4 | 9.4E3 | 8.6E3 | <10 | <10 | <10 |
| Wk 3 | 1.6E4 | 4.8E3 | 7.6E3 | <10 | <10 | <10 |
| Wk 4 | 1.1E4 | 5.0E3 | 5.8E3 | <10 | <10 | <10 |

TABLE 12

Microbial test results for diesel fuel with biocide (FUELSAVER ™) only

|      | 19. FS 135 ppm (Control) | | | 20. FS 1000 ppm (Control) | | |
|------|---------------|--------------|------------|---------------|--------------|------------|
| Time | Ps. aeruginosa | Y. tropicalis | H. resinae | Ps. aeruginosa | Y. tropicalis | H. resinae |
| Day 0 | 3.7E6 | 2.8E5 | 5.3E5 | 3.7E6 | 2.8E5 | 5.3E5 |
| Wk 1 | 4.0E4 | 5.7E4 | 5.0E4 | 1.9E2 | 8.6E2 | 2.2E3 |
| Wk 2 | 2.2E4 | 9.6E3 | 4.0E4 | <10 | <10 | 6.7E2 |
| Wk 3 | 4.8E3 | 7.0E3 | 8.6E3 | <10 | <10 | 1.6E2 |
| Wk 4 | 8.0E3 | 6.4E3 | 7.2E3 | <10 | <10 | 2.2E2 |

TABLE 13

Microbial test results for diesel fuel only

| | 21. No biocides or amines (Control) | | |
|---|---|---|---|
| Time | Ps. aeruginosa | Y. tropicalis | H. resinae |
| Day 0 | 3.7E6 | 2.8E5 | 5.3E5 |
| Wk 1 | 8.8E6 | 7.3E5 | 3.8E5 |
| Wk 2 | 4.2E7 | 7.0E6 | 6.2E5 |
| Wk 3 | 7.3E7 | 8.2E6 | 4.4E6 |
| Wk 4 | 2.4E7 | 7.3E6 | 2.3E6 |

TABLE 14

Microbial test results for biodiesel fuel with a) aminoalcohol, b) biocide (FUELSAVER ™), and c) aminoalcohol and biocide

| AOctM (ppm) | ACyHM (ppm) | Biocide (ppm) | Week 1 Ps. aeruginosa | Week 1 Y. tropicalis | Week 1 H. resinae | Week 2 Ps. aeruginosa | Week 2 Y. tropicalis |
|---|---|---|---|---|---|---|---|
| 0 | 0 | 0 | 3.80E+06 | 4.40E+05 | 5.80E+05 | 1.20E+07 | 2.70E+06 |
| 0 | 0 | 250 | 1.80E+05 | 8.30E+04 | 1.10E+05 | 9.40E+04 | 4.80E+05 |
| 0 | 0 | 500 | 8.80E+04 | 6.00E+04 | 8.40E+04 | 3.80E+04 | 1.00E+05 |
| 0 | 0 | 1000 | 4.80E+04 | 2.30E+04 | 5.50E+04 | 8.60E+03 | 6.20E+04 |
| 1500 | 0 | 0 | <1.0E2 | <1.0E2 | <1.0E2 | <1.0E2 | <1.0E2 |
| 3000 | 0 | 0 | <1.0E2 | <1.0E2 | <1.0E2 | <1.0E2 | <1.0E2 |
| 1500 | 0 | 250 | <1.0E2 | <1.0E2 | <1.0E2 | <1.0E2 | <1.0E2 |
| 1500 | 0 | 500 | <1.0E2 | <1.0E2 | <1.0E2 | <1.0E2 | <1.0E2 |
| 3000 | 0 | 250 | <1.0E2 | <1.0E2 | <1.0E2 | <1.0E2 | <1.0E2 |
| 3000 | 0 | 500 | <1.0E2 | <1.0E2 | <1.0E2 | <1.0E2 | <1.0E2 |
| 0 | 1500 | 0 | <1.0E2 | <1.0E2 | <1.0E2 | <1.0E2 | <1.0E2 |
| 0 | 3000 | 0 | <1.0E2 | <1.0E2 | <1.0E2 | <1.0E2 | <1.0E2 |
| 0 | 1500 | 250 | <1.0E2 | <1.0E2 | <1.0E2 | <1.0E2 | <1.0E2 |
| 0 | 1500 | 500 | <1.0E2 | <1.0E2 | <1.0E2 | <1.0E2 | <1.0E2 |
| 0 | 3000 | 250 | <1.0E2 | <1.0E2 | <1.0E2 | <1.0E2 | <1.0E2 |
| 0 | 3000 | 500 | <1.0E2 | <1.0E2 | <1.0E2 | <1.0E2 | <1.0E2 |

| Week 2 H. resinae | Week 3 Ps. aeruginosa | Week 3 Y. tropicalis | Week 3 H. resinae | Week 4 Ps. aeruginosa | Week 4 Y. tropicalis | Week 4 H. resinae |
|---|---|---|---|---|---|---|
| 2.20E+06 | 8.80E+06 | 1.80E+07 | 5.20E+06 | 9.20E+06 | 7.30E+06 | 8.50E+05 |
| 3.20E+05 | 5.40E+04 | 3.80E+05 | 3.30E+05 | 9.40E+04 | 6.40E+04 | 4.20E+05 |
| 6.70E+04 | 8.20E+03 | 7.70E+04 | 7.00E+04 | 1.60E+04 | 2.70E+04 | 6.00E+04 |
| 1.20E+04 | 6.70E+02 | 3.40E+04 | 6.80E+03 | 8.80E+03 | 5.70E+03 | 7.20E+03 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | 1.30E+04 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |
| <1.0E2 | <1.0E2 | <1.0E2 | <1.0E2 | <1.0E2 | <1.0E2 | <1.0E2 |

TABLE 15

Bacteria (*Ps. aeruginosa*) test results for biodiesel fuel with a) aminoalcohol, b) aminoalcohol salts, c) oleic acid, and d) potassium oleate

| AOctM/ Oleic (ppm) | KOH/ Oleic (ppm) | TEA/ Oleic (ppm) | AOctM/ Acetate (ppm) | AOctM (ppm) | Oleic Acid (ppm) | TEA (ppm) | Week 1 Bact/ml | Week 2 Bact/ml | Week 3 Bact/ml | Week 4 Bact/ml | Week 5 Bact/ml | Week 6 Bact/ml | Week 7 Bact/ml | Week 8 Bact/ml | Week 9 Bact/ml | Week 10 Bact/ml | Week 11 Bact/ml | Week 12 Bact/ml | Week 14 Bact/ml |
|---|---|---|---|---|---|---|---|---|---|---|---|---|---|---|---|---|---|---|---|
| 0 | 0 | 0 | 0 | 0 | 0 | 0 | 3.70E+06 | 5.60E+06 | 6.20E+06 | 3.80E+07 | | | | | | | | | |
| 100 | 0 | 0 | 0 | 0 | 0 | 0 | 2.00E+06 | 4.80E+06 | 8.00E+06 | 4.30E+06 | | | | | | | | | |
| 500 | 0 | 0 | 0 | 0 | 0 | 0 | 7.60E+05 | 8.00E+06 | 5.40E+06 | 2.10E+06 | | | | | | | | | |
| 1500 | 0 | 0 | 0 | 0 | 0 | 0 | <1.0E2 | <1.0E2 | <1.0E2 | <1.0E2 | <1.0E2 | <1.0E2 | <1.0E2 | <1.0E2 | <1.0E2 | <1.0E2 | <1.0E2 | <1.0E2 | 8.00E+05 |
| 0 | 500 | 0 | 0 | 0 | 0 | 0 | 3.80E+03 | 2.50E+04 | 9.30E+04 | 4.50E+05 | | | | | | | | | |
| 0 | 1500 | 0 | 0 | 0 | 0 | 0 | 9.80E+02 | 4.70E+04 | 6.20E+04 | 3.20E+04 | | | | | | | | | |
| 0 | 0 | 500 | 0 | 0 | 0 | 0 | 7.30E+04 | 5.00E+05 | 1.20E+06 | 1.10E+06 | | | | | | | | | |
| 0 | 0 | 1500 | 0 | 0 | 0 | 0 | 2.00E+03 | 9.00E+04 | 2.20E+05 | 8.30E+04 | | | | | | | | | |
| 0 | 0 | 0 | 500 | 0 | 0 | 0 | 9.70E+04 | 5.60E+05 | 7.60E+05 | 6.70E+05 | | | | | | | | | |
| 0 | 0 | 0 | 1500 | 0 | 0 | 0 | 6.60E+04 | 2.30E+05 | 9.00E+02 | 1.20E+04 | | | | | | | | | |
| 0 | 0 | 0 | 0 | 100 | 0 | 0 | 2.30E+05 | 5.60E+05 | 3.60E+05 | 2.80E+04 | | | | | | | | | |
| 0 | 0 | 0 | 0 | 500 | 0 | 0 | 2.20E+03 | 2.00E+02 | <1.0E2 | 1.30E+03 | 4.70E+03 | 6.50E+03 | 3.20E+05 | 4.1E+04 | 6.10E+05 | 1.70E+06 | 7.90E+06 | 6.10E+06 | |
| 0 | 0 | 0 | 0 | 1500 | 0 | 0 | <1.0E2 | <1.0E2 | <1.0E2 | <1.0E2 | <1.0E2 | <1.0E2 | <1.0E2 | <1.0E2 | <1.0E2 | <1.0E2 | <1.0E2 | <1.0E2 | <1.0E2 |
| 0 | 0 | 0 | 0 | 0 | 500 | 0 | 7.80E+05 | 8.80E+05 | 7.40E+05 | 8.00E+05 | | | | | | | | | |
| 0 | 0 | 0 | 0 | 0 | 1500 | 0 | 5.00E+04 | 2.00E+05 | 1.30E+05 | 3.20E+05 | | | | | | | | | |
| 0 | 0 | 0 | 0 | 0 | 0 | 500 | 1.80E+06 | 3.00E+06 | 2.40E+06 | 9.00E+05 | | | | | | | | | |
| 0 | 0 | 0 | 0 | 0 | 0 | 1500 | 4.00E+05 | 7.60E+05 | 8.20E+05 | 5.70E+05 | | | | | | | | | |

TABLE 16

Yeast (*Y. tropcalis*) test results for biodiesel fuel with a) aminoalcohol, b) aminoalcohol salts, c) oleic acid, and d) potassium oleate

| AOctM/ Oleic (ppm) | KOH/ Oleic (ppm) | TEA/ Oleic (ppm) | AOctM/ Acetate (ppm) | AOctM (ppm) | Oleic Acid (ppm) | TEA (ppm) | Week 1 Yeast/ml | Week 2 Yeast/ml | Week 3 Yeast/ml |
|---|---|---|---|---|---|---|---|---|---|
| 0 | 0 | 0 | 0 | 0 | 0 | 0 | 5.60E+02 | 8.20E+03 | 5.60E+03 |
| 100 | 0 | 0 | 0 | 0 | 0 | 0 | 1.10E+02 | 3.70E+04 | 5.60E+04 |
| 500 | 0 | 0 | 0 | 0 | 0 | 0 | 3.20E+02 | 9.20E+03 | 5.00E+03 |
| 1500 | 0 | 0 | 0 | 0 | 0 | 0 | <1.0E2 | <1.0E2 | <1.0E2 |
| 0 | 500 | 0 | 0 | 0 | 0 | 0 | 9.00E+02 | 1.20E+03 | 2.00E+03 |
| 0 | 1500 | 0 | 0 | 0 | 0 | 0 | <1.0E2 | <1.0E2 | 1.10E+02 |
| 0 | 0 | 500 | 0 | 0 | 0 | 0 | 2.30E+05 | 6.60E+04 | 7.80E+03 |
| 0 | 0 | 1500 | 0 | 0 | 0 | 0 | 9.70E+02 | 4.20E+02 | 3.80E+02 |
| 0 | 0 | 0 | 500 | 0 | 0 | 0 | 8.00E+03 | 9.00E+03 | 6.00E+03 |
| 0 | 0 | 0 | 1500 | 0 | 0 | 0 | 3.70E+04 | 1.20E+04 | 4.20E+03 |
| 0 | 0 | 0 | 0 | 100 | 0 | 0 | 6.70E+03 | 7.20E+03 | 5.70E+03 |
| 0 | 0 | 0 | 0 | 500 | 0 | 0 | 8.80E+02 | 1.10E+02 | <1.0E2 |
| 0 | 0 | 0 | 0 | 1500 | 0 | 0 | <1.0E2 | <1.0E2 | <1.0E2 |
| 0 | 0 | 0 | 0 | 0 | 500 | 0 | 6.00E+04 | 4.50E+04 | 2.40E+04 |
| 0 | 0 | 0 | 0 | 0 | 1500 | 0 | 1.70E+04 | 3.70E+04 | 5.00E+04 |
| 0 | 0 | 0 | 0 | 0 | 0 | 500 | 8.80E+03 | 6.00E+03 | 2.00E+04 |
| 0 | 0 | 0 | 0 | 0 | 0 | 1500 | <1.0E2 | <1.0E2 | <1.0E2 |

TABLE 16-continued

Yeast (*Y. tropcalis*) test results for biodiesel fuel with a) aminoalcohol, b) aminoalcohol salts, c) oleic acid, and d) potassium oleate

| Week 4 Yeast/ml | Week 5 Yeast/ml | Week 6 Yeast/ml | Week 7 Yeast/ml | Week 8 Yeast/ml | Week 9 Yeast/ml | Week 10 Yeast/ml | Week 11 Yeast/ml | Week 12 Yeast/ml | Week 14 Yeast/ml |
|---|---|---|---|---|---|---|---|---|---|
| 4.80E+03 | | | | | | | | | |
| 3.00E+04 | | | | | | | | | |
| 3.90E+03 | | | | | | | | | |
| <1.0E2 | <1.0E2 | <1.0E2 | <1.0E2 | <1.0E2 | <1.0E2 | <1.0E2 | <1.0E2 | <1.0E2 | 8.80E+03 |
| 1.80E+03 | | | | | | | | | |
| 3.70E+02 | | | | | | | | | |
| 9.20E+03 | | | | | | | | | |
| 5.00E+02 | | | | | | | | | |
| 8.20E+03 | | | | | | | | | |
| 5.80E+03 | | | | | | | | | |
| 4.70E+03 | | | | | | | | | |
| <1.0E2 | <1.0E2 | <1.0E2 | <1.0E2 | <1.0E2 | <1.0E2 | 2.10E+04 | 4.70E+05 | 7.10E+05 | |
| <1.0E2 | <1.0E2 | <1.0E2 | <1.0E2 | <1.0E2 | <1.0E2 | <1.0E2 | <1.0E2 | <1.0E2 | <1.0E2 |
| 3.00E+04 | | | | | | | | | |
| 1.20E+04 | | | | | | | | | |
| 4.20E+04 | | | | | | | | | |
| 1.30E+02 | | | | | | | | | |

TABLE 17

Mold (*H. resinae*) test results for biodiesel fuel with a) aminoalcohol, b) aminoalcohol salts, c) oleic acid, and d) potassium oleate

| AOctM/Oleic (ppm) | KOH/Oleic (ppm) | TEA/Oleic (ppm) | AOctM/Acetate (ppm) | AOctM (ppm) | Oleic Acid (ppm) | TEA (ppm) | Week 1 Mold/ml | Week 2 Mold/ml | Week 3 Mold/ml |
|---|---|---|---|---|---|---|---|---|---|
| 0 | 0 | 0 | 0 | 0 | 0 | 0 | 8.00E+03 | 2.20E+04 | 7.60E+03 |
| 100 | 0 | 0 | 0 | 0 | 0 | 0 | 5.30E+02 | 1.30E+06 | 1.20E+04 |
| 500 | 0 | 0 | 0 | 0 | 0 | 0 | 2.00E+02 | 4.50E+04 | 6.70E+04 |
| 1500 | 0 | 0 | 0 | 0 | 0 | 0 | <1.0E2 | <1.0E2 | <1.0E2 |
| 0 | 500 | 0 | 0 | 0 | 0 | 0 | 3.80E+03 | 2.70E+04 | 1.20E+04 |
| 0 | 1500 | 0 | 0 | 0 | 0 | 0 | <1.0E2 | <1.0E2 | 2.30E+03 |
| 0 | 0 | 500 | 0 | 0 | 0 | 0 | 8.20E+04 | 3.70E+05 | 4.30E+05 |
| 0 | 0 | 1500 | 0 | 0 | 0 | 0 | 3.70E+02 | 1.30E+04 | 2.00E+04 |
| 0 | 0 | 0 | 500 | 0 | 0 | 0 | 7.70E+03 | 5.30E+04 | 7.80E+04 |
| 0 | 0 | 0 | 1500 | 0 | 0 | 0 | 1.40E+05 | 3.30E+05 | 1.10E+05 |
| 0 | 0 | 0 | 0 | 100 | 0 | 0 | 2.10E+02 | 1.10E+04 | 2.80E+06 |
| 0 | 0 | 0 | 0 | 500 | 0 | 0 | <1.0E2 | <1.0E2 | <1.0E2 |
| 0 | 0 | 0 | 0 | 1500 | 0 | 0 | <1.0E2 | <1.0E2 | <1.0E2 |
| 0 | 0 | 0 | 0 | 0 | 500 | 0 | 1.70E+05 | 6.00E+05 | 8.20E+05 |
| 0 | 0 | 0 | 0 | 0 | 1500 | 0 | 6.40E+04 | 7.70E+05 | 6.00E+05 |
| 0 | 0 | 0 | 0 | 0 | 0 | 500 | 2.30E+04 | 1.20E+05 | 1.70E+06 |
| 0 | 0 | 0 | 0 | 0 | 0 | 1500 | <1.0E2 | 2.30E+02 | 4.20E+03 |

| Week 4 Mold/ml | Week 5 Mold/ml | Week 6 Mold/ml | Week 7 Mold/ml | Week 8 Mold/ml | Week 9 Mold/ml | Week 10 Mold/ml | Week 11 Mold/ml | Week 12 Mold · mL | Week 14 Mold · mL |
|---|---|---|---|---|---|---|---|---|---|
| 7.00E+03 | | | | | | | | | |
| 3.40E+04 | | | | | | | | | |
| 5.00E+04 | | | | | | | | | |
| <1.0E2 | <1.0E2 | <1.0E2 | <1.0E2 | <1.0E2 | <1.0E2 | <1.0E2 | <1.0E2 | <1.0E2 | 2.80E+04 |
| 5.00E+03 | | | | | | | | | |
| <1.0E2 | | | | | | | | | |
| 6.20E+05 | | | | | | | | | |
| 4.70E+03 | | | | | | | | | |
| 4.50E+04 | | | | | | | | | |
| 2.40E+05 | | | | | | | | | |
| 7.60E+05 | | | | | | | | | |
| 2.00E+02 | 6.80E+02 | 5.60E+02 | 1.70E+02 | 2.20E+02 | 4.10E+02 | 3.40E+04 | 8.00E+05 | | |
| <1.0E2 | <1.0E2 | <1.0E2 | <1.0E2 | <1.0E2 | <1.0E2 | <1.0E2 | <1.0E2 | <1.0E2 | <1.0E2 |
| 7.80E+03 | | | | | | | | | |
| 9.80E+03 | | | | | | | | | |
| 1.60E+03 | | | | | | | | | |
| 5.60E+02 | | | | | | | | | |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A blend comprising:
 a hydrocarbonaceous composition;
 a corrosion inhibitory amount of an aminoalcohol that is:
  1-aminocyclohexylmethanol or a mixture of 2-amino-2-methyl-1-octanol, 2-amino-2-ethyl-1-heptanol, and 2-amino-2-propyl-1-hexanol,
 or salt thereof; and
 a biocidally effective amount of a biocide that is a blend of 4-(2-nitrobutyl)-morpholine and 4,4'-(2-ethyl-2-nitrotrimethylene) dimorpholine.

* * * * *